(12) United States Patent
Stalcup et al.

(10) Patent No.: US 6,332,894 B1
(45) Date of Patent: Dec. 25, 2001

(54) POLYMER FILLED SPINAL FUSION CAGE

(75) Inventors: Gregory C Stalcup, Columbia City; Antony J. Lozier, Warsaw, both of IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/520,893

(22) Filed: Mar. 7, 2000

(51) Int. Cl.$^7$ .................................................. A61B 17/70
(52) U.S. Cl. ..................................... 623/17.11; 623/23.58
(58) Field of Search ............................ 623/17.12, 23.58, 623/23.63, 17.11

(56) References Cited

U.S. PATENT DOCUMENTS

| | | | |
|---|---|---|---|
| 4,313,434 | 2/1982 | Segal . | |
| 4,645,503 | * 2/1987 | Lin et al. | 623/23.58 |
| 4,662,887 | 5/1987 | Turner et al. . | |
| 4,705,519 | * 11/1987 | Hayes et al. | 623/23.58 |
| 4,714,478 | 12/1987 | Fischer . | |
| 4,728,570 | * 3/1988 | Ashman et al. | 623/23.58 |
| 5,092,888 | * 3/1992 | Iwamoto et al. | 623/23.58 |
| 5,102,413 | 4/1992 | Poddar | 606/62 |
| 5,192,326 | * 3/1993 | Bao et al. | 623/17.12 |
| 5,303,718 | 4/1994 | Krajicek | 128/897 |
| 5,423,850 | 6/1995 | Berger | 606/192 |
| 5,480,400 | 1/1996 | Berger | 606/60 |
| 5,496,371 | * 3/1996 | Eppley et al. | 623/17.18 |
| 5,514,137 | 5/1996 | Coutts | 606/62 |
| 5,571,189 | * 11/1996 | Kuslich | 623/17.12 |
| 5,658,310 | 8/1997 | Berger | 606/192 |
| 5,681,289 | 10/1997 | Wilcox et al. | 604/175 |
| 5,827,289 | 10/1998 | Reiley et al. | 606/86 |
| 5,888,220 | * 3/1999 | Felt et al. | 623/23.72 |
| 5,951,160 | 9/1999 | Ronk | 366/130 |
| 5,997,582 | 12/1999 | Weiss . | |
| 6,022,376 | * 2/2000 | Assell et al. | 623/17.12 |

* cited by examiner

Primary Examiner—Paul J. Hirsch
(74) Attorney, Agent, or Firm—Todd A. Dawson

(57) ABSTRACT

An orthopaedic implant for implanting between adjacent vertebrae and a spine, includes a generally annular bag; and a hardened polymer with the bag. The method of fusing adjacent vertebrae in a spine includes the steps of forming an access hole in an annulus of a disc between the adjacent vertebrae; removing the nucleus within the disc to form a cavity surrounded by the annulus; placing a generally annular bag within the cavity; filling the bag with a polymer; injecting bone particles into the cavity surrounded by the annular bag; and hardening the polymer.

22 Claims, 9 Drawing Sheets

POLYMER FILLED SPINAL FUSION CAGE

BACKGROUND OF THE INVENTION

1. Field of the Invention

The present invention relates to orthopaedic implants, and, more particularly, to spinal fusion devices.

2. Description of the Related Art

Spinal fusion typically involves fusion between two adjacent vertebrae by removing a disc between two adjacent vertebrae and placing a cage between the vertebrae. The patient may be cut both on the anterior and posterior sides (stomach and back) and the disc removed from between the two adjacent vertebrae. The disc includes an annulus which surrounds a nucleus. The annulus is torn, cut or otherwise removed from between the vertebrae and the softer nucleus also removed. A cage is placed between the vertebrae where the disc is removed and a bone graft including bone particles is packed within the cage and extends between the end plates of the adjacent vertebrae. Rods may also be placed on the posterior side of the spine, with screws attached to a respective rod and extending into a respective vertebrae.

SUMMARY OF THE INVENTION

The present invention provides an orthopaedic implant including a bag which is placed within a cavity surrounded by an annulus of a disc and which includes a central cavity. The bag is filled with a polymer, and the central cavity defined by the bag is filled with a bone particle and polymer matrix.

The invention comprises, in one form thereof, an orthopaedic implant for implanting between adjacent vertebrae in a spine, including a generally annular bag; and a hardened polymer within the bag.

The invention comprises, in another form thereof, a method of fusing adjacent vertebrae in a spine, including the steps of forming an access hole in an annulus of a disc between the adjacent vertebrae; removing the nucleus within the disc to form a cavity surrounded by the annulus; placing a generally annular bag within the cavity; filling the bag with a polymer; injecting bone particles into the cavity surrounded by the annular bag and hardening the polymer.

An advantage of the present invention is that an orthopaedic implant may be implanted between adjacent vertebrae in a spine in a minimal evasive surgery technique.

Another advantage is that the ligaments and tendons surrounding the spine may be properly tensioned.

Yet another advantage is that the patient may begin loading the implant soon after surgery.

A still further advantage is that the implant may be implanted from a single posterior incision location, or may be implanted from a posterior and/or anterior incision location.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
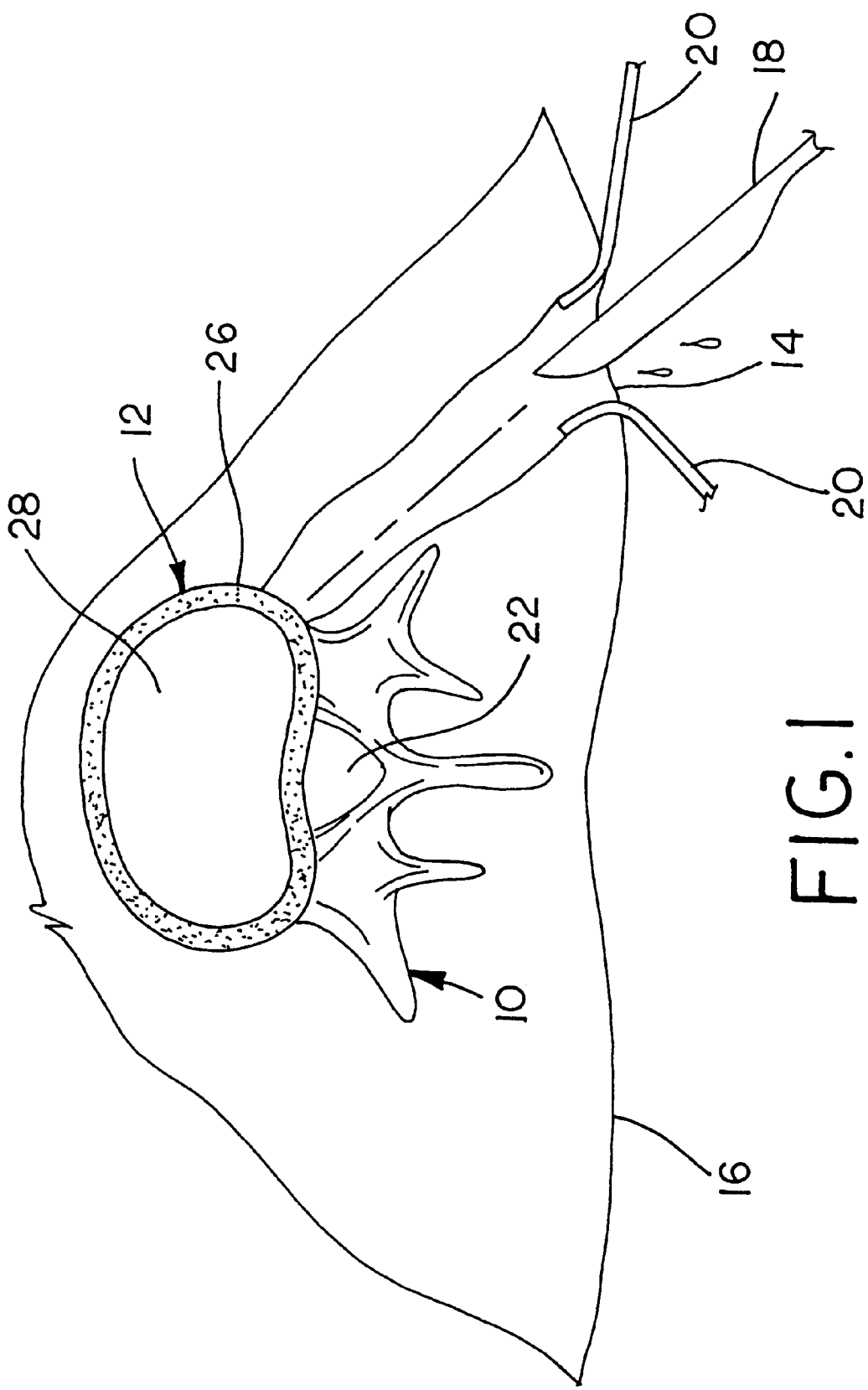
FIG. 1 is a fragmentary, sectional view of a vertebrae and disc, illustrating an orientation and size of an incision made relative thereto.

Referring now to the drawings, an embodiment of the method of the present invention for fusing adjacent vertebrae in a spine will be described hereinafter. The spine includes a plurality of adjacent vertebrae 10, which each adjacent pair of vertebrae 10 being separated by a disc 12. A disc 12 may become damaged because of a number of reasons, thus requiring the fusion of adjacent vertebrae.

Figure 2:
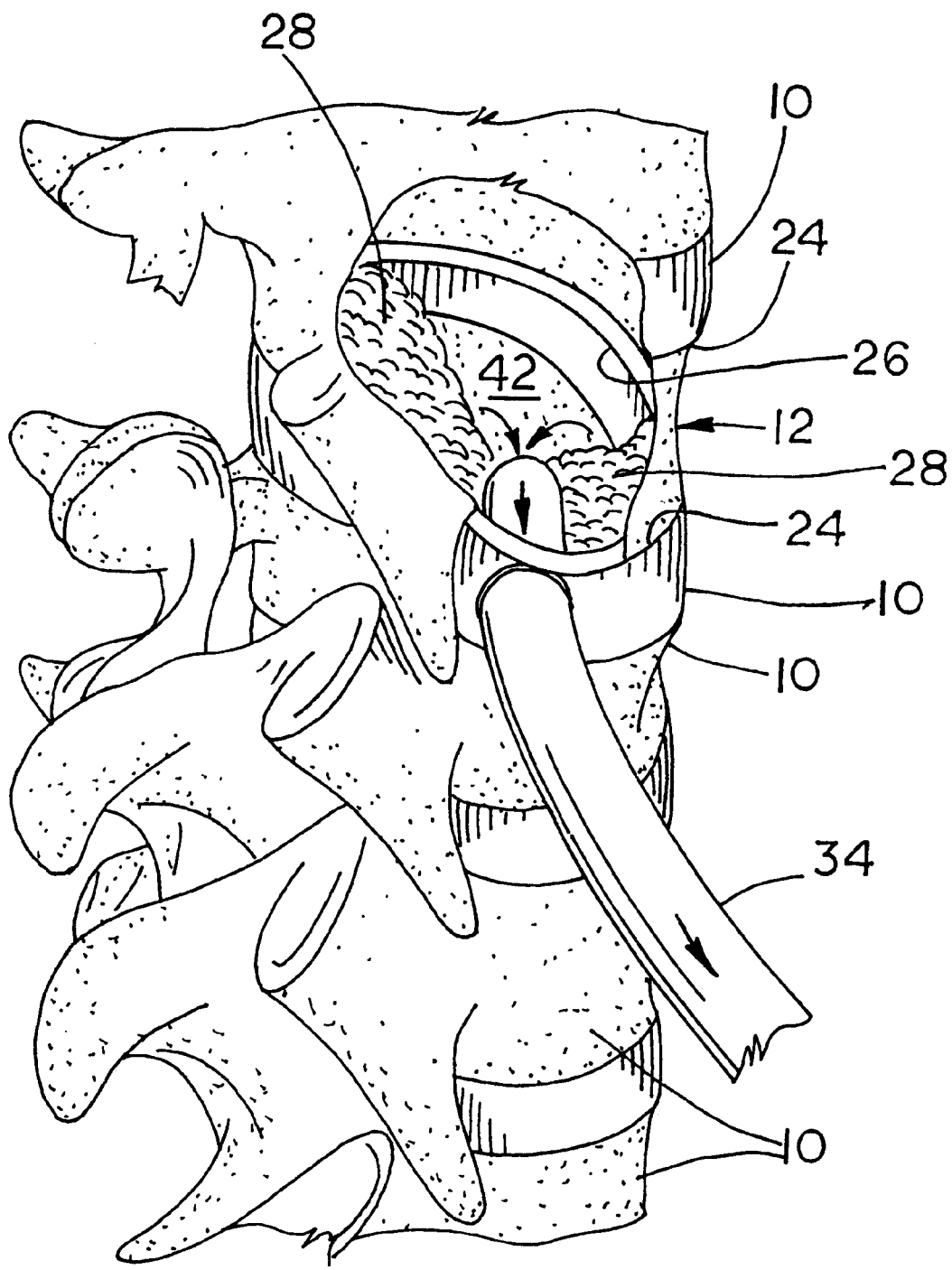
FIG. 2 is a perspective view illustrating evacuation of a nucleus within a disc.

FIG. 1 illustrates a fragmentary, sectional view of a spine as viewed in a direction parallel to the spine of a patient. Disc 12 is assumed to be damaged to an extent requiring fusion between adjacent vertebrae 10. Referring to FIG. 2., each vertebrae 10 includes oppositely facing end plates 24 on each longitudinal end thereof. Each disc 12 is interposed between a pair of adjacent vertebrae, and includes an annulus 26 surrounding a nucleus 28.

An incision 14 is made in the back 16 of the patient using a scalpel 18 or other appropriate cutting instrument. Incision 14 may be held open using suitable instrumentation 20. Incision 14 is made at an angle approximately as shown to disc 12, thereby avoiding an area 22 where the spinal cord is located. After incision 14 is made, an access hole 30 is formed in an annulus 26 of a selected disc 12 by known methods such as a drill bit or scalpel. Since incision 14 is formed in the back 16 of the patient, access hole 30 generally is formed in the posterior side of disc 12.

Figure 3:
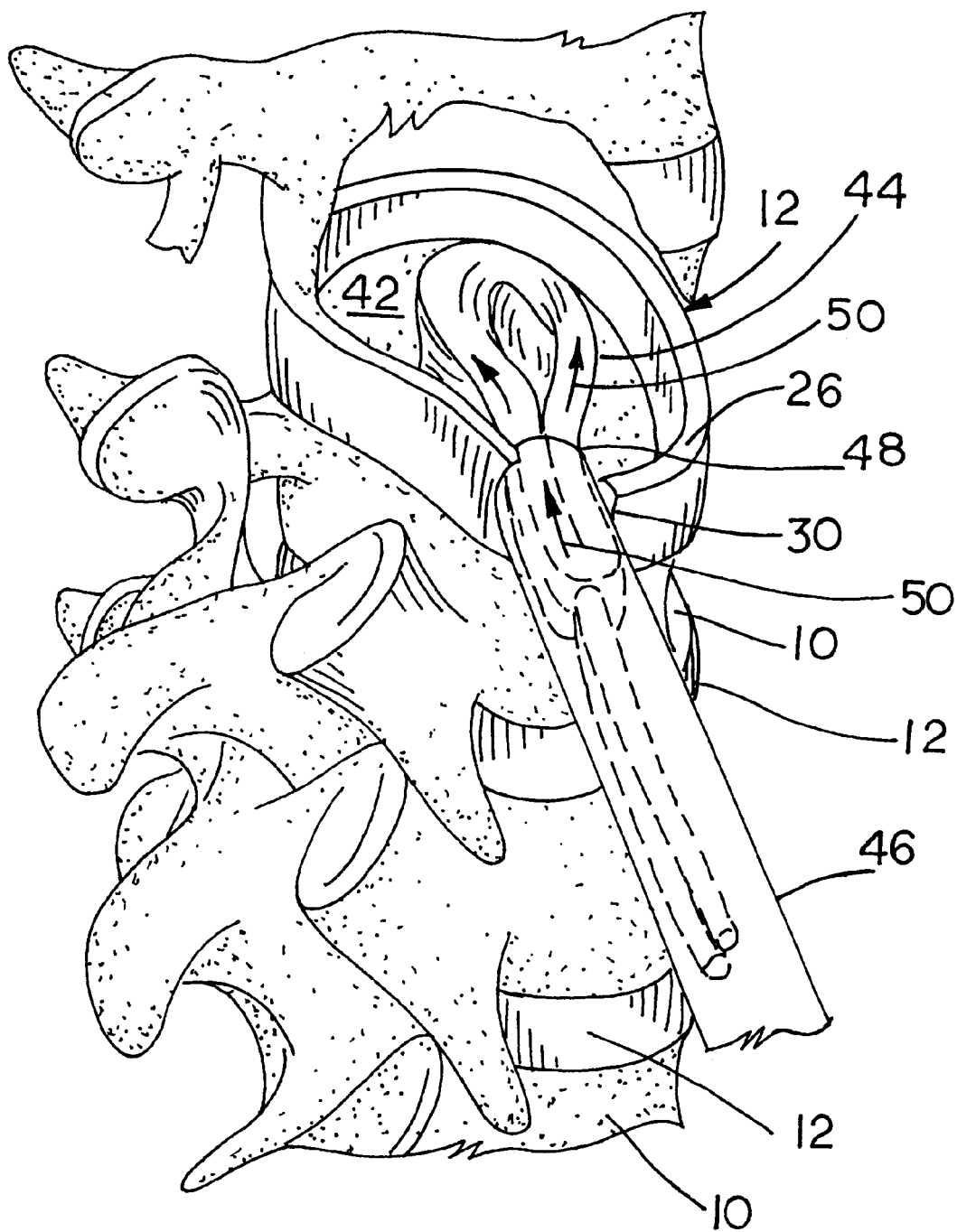
FIG. 3 is a perspective view illustrating placement of an annular bag within a disc.

After formation of access hole 30, the nucleus 28 is evacuated from within disc 12 (FIG. 3). A vacuum tube 34 or the like may be used to remove nucleus 28. Removal of nucleus 28 causes the formation of a cavity 42 within disc 12 surrounded by annulus 26. Vacuum tube 34 is removed from cavity 42 and incision 14 after evacuation of nucleus 28.

Figure 4:
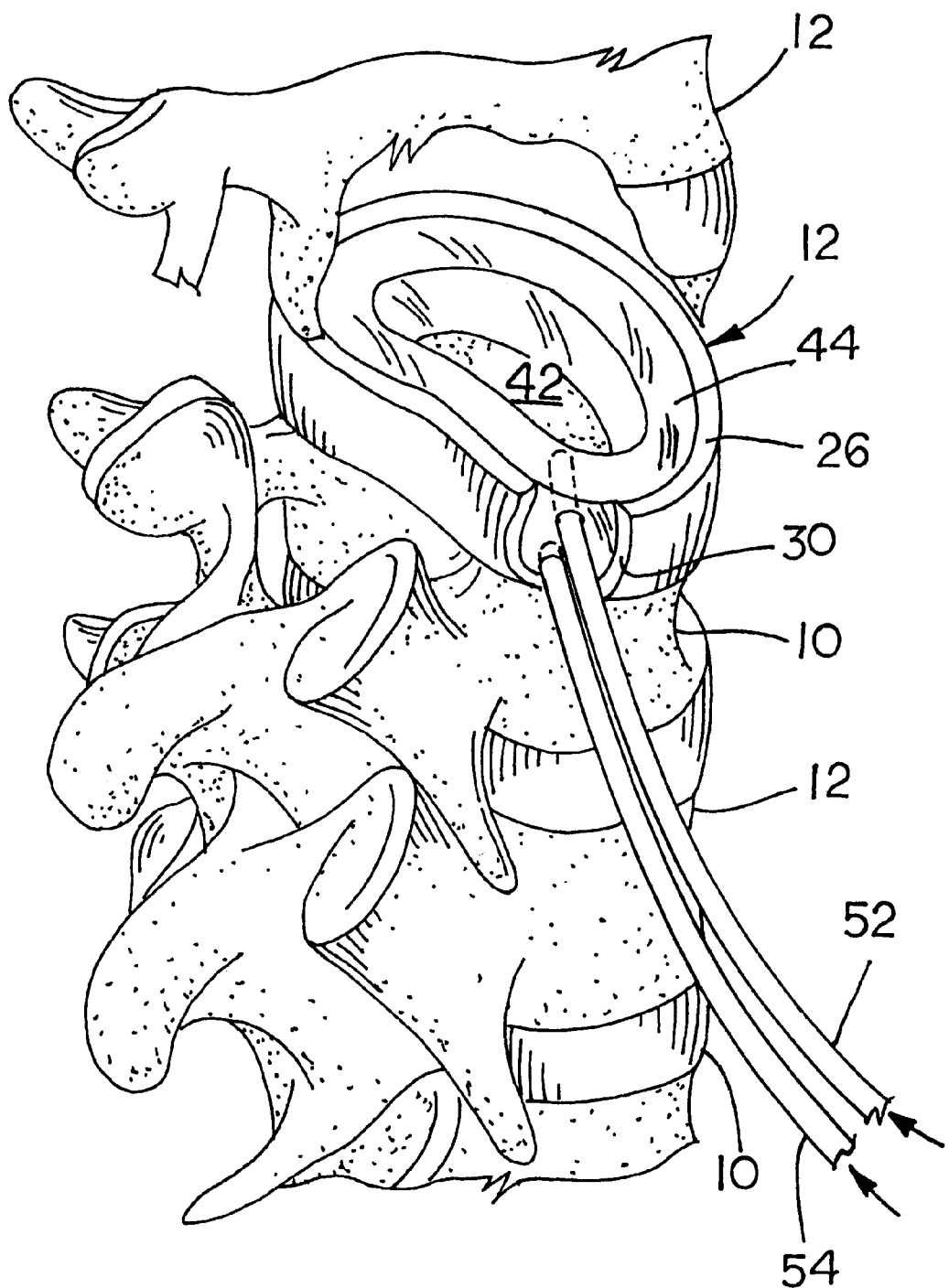
FIG. 4 is a perspective view of the bag in a relaxed state after being placed within the disc.

A flexible bag 44 having a generally annular shape when in a relaxed state is then inserted within cavity 42 (FIG. 4). More particularly, bag 44 is folded and inserted within a pre-load tube 46. Pre-load tube 46 has an outside diameter which is slightly smaller than the inside diameter of access hole 30 formed in annulus 26. Pre-load tube 46, with bag 44 loaded therein, is inserted into incision 14 and access hole 30 such that an end 48 of pre-load tube 46 extends through access hole 30 and into cavity 42. Bag 44 is then slid out of pre-load tube 46 and into cavity 42 as indicated by arrows 50. Bag 44 may be ejected from pre-load tube 46 in any suitable manner, such as by utilizing a plunger (not shown) disposed within pre-load tube 46 having an outside diameter which is slightly smaller than the inside diameter of pre-load tube 46.

Figure 5:
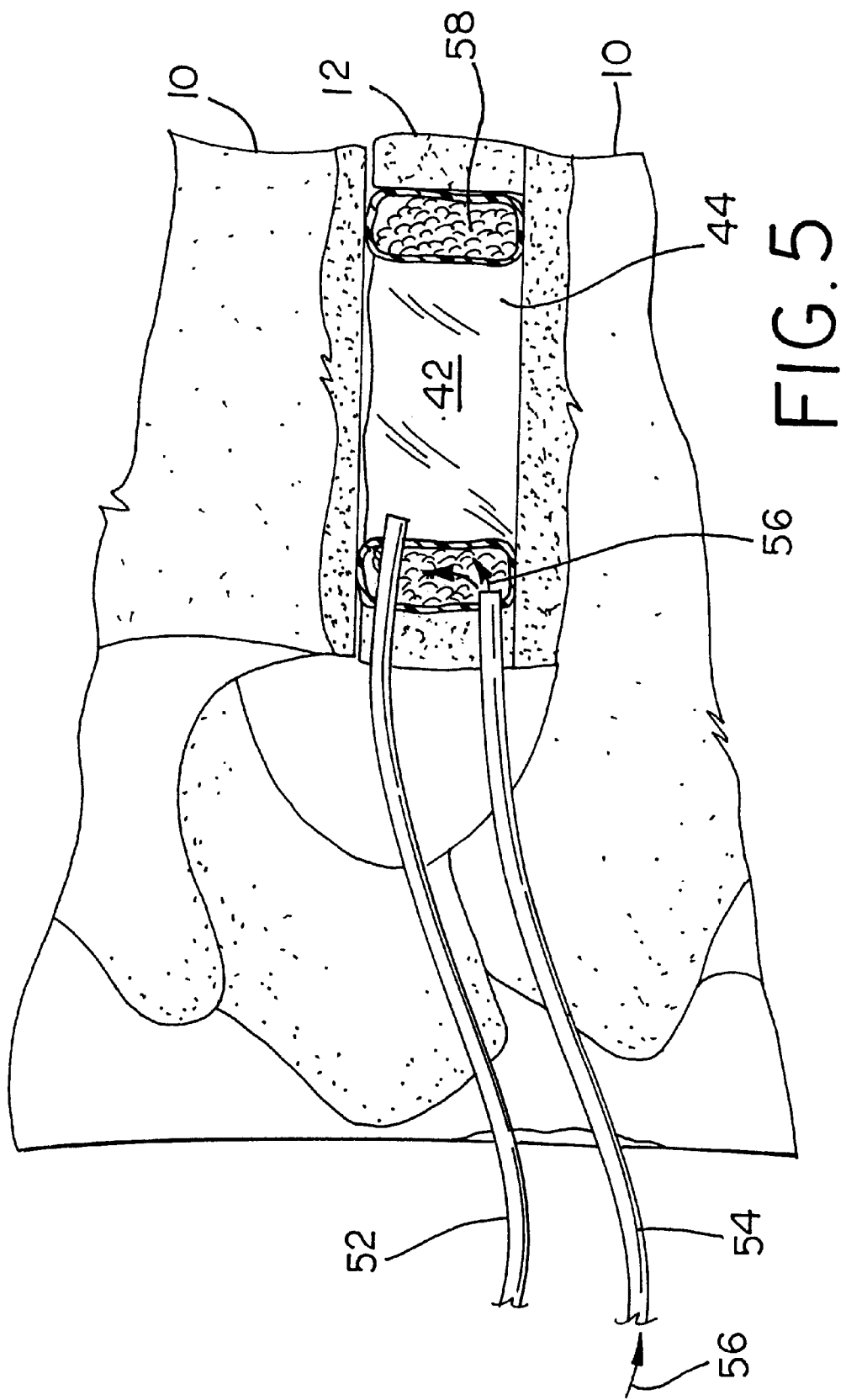
FIG. 5 is a side, sectional view of the bag while being filled with a polymer to a first predetermined amount.
Figure 6:
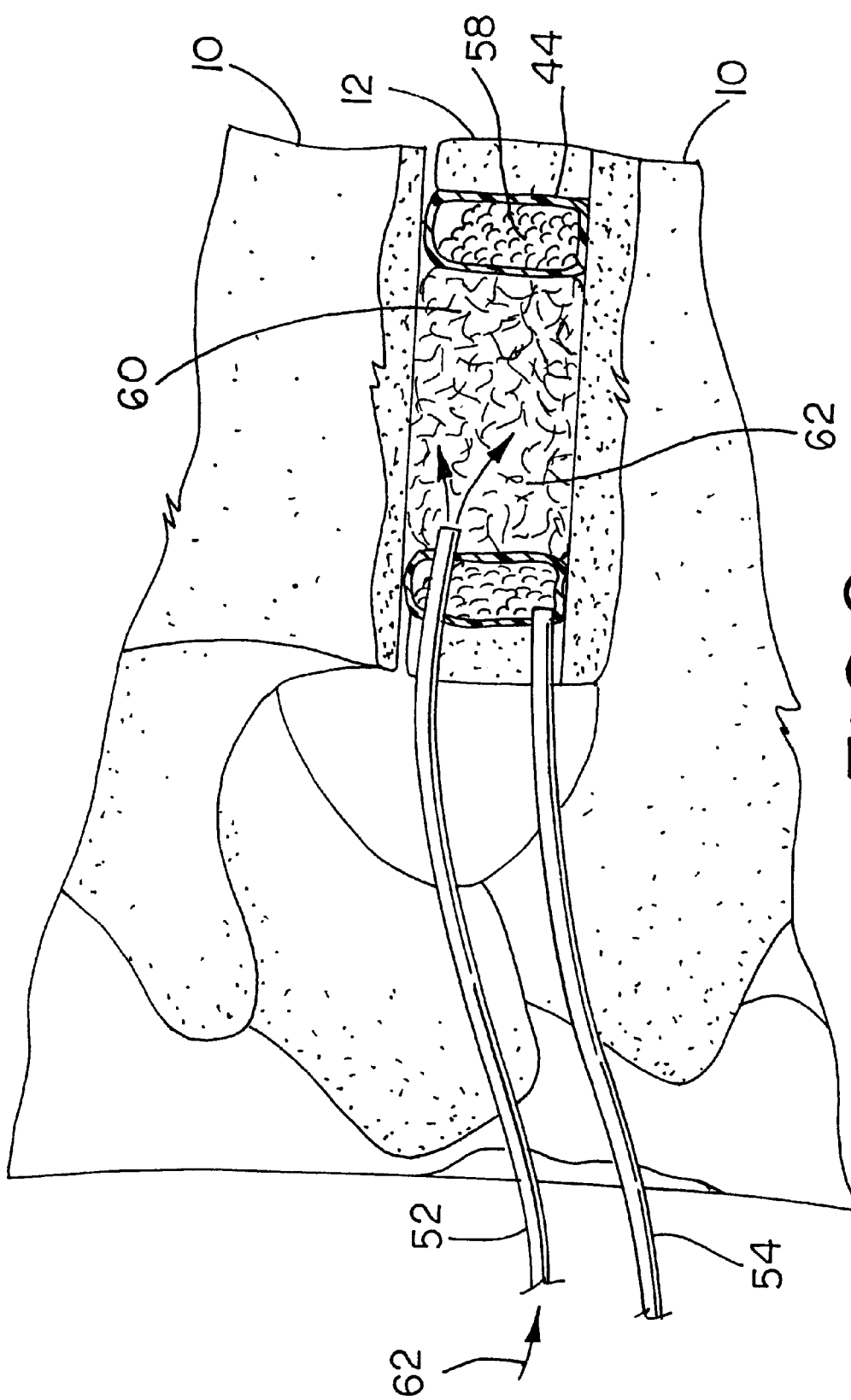
FIG. 6 is a side, sectional view illustrating a bone particle and polymer matrix being injected into a cavity surrounded by the bag.

Bag 44 is selected with a size and shape to generally fill the perimeter of cavity 42 when disposed therein (FIG. 5). A first fill hose 52 and a second fill hose 54 are each attached to bag 44 (FIGS. 5–11). First fill hose 52 extends through bag 44 and terminates in a portion of cavity 42 surrounded by bag 44 (FIG. 6). On the other hand, second fill hose 54 extends into and terminates within bag 44. A high strength polymer is injected within bag 44 through second fill hose 54, as indicated by arrows 56. During this first fill stage of bag 44, the polymer 58 is injected to substantially fill bag 44 to a first predetermined amount without expanding or deforming bag 44. In the embodiment shown, bag 44 is porous and polymer 58 is in the form of a bioresorbable and curable polymer, some of which passes through bag 44. The curing can be effected by the application of energy such as thermal energy, light energy, or X-ray energy, or the addition of a chemical catalyst. During the first fill stage of bag 44 shown in FIG. 6, polymer 58 preferably remains in an uncured state.

Figure 7:
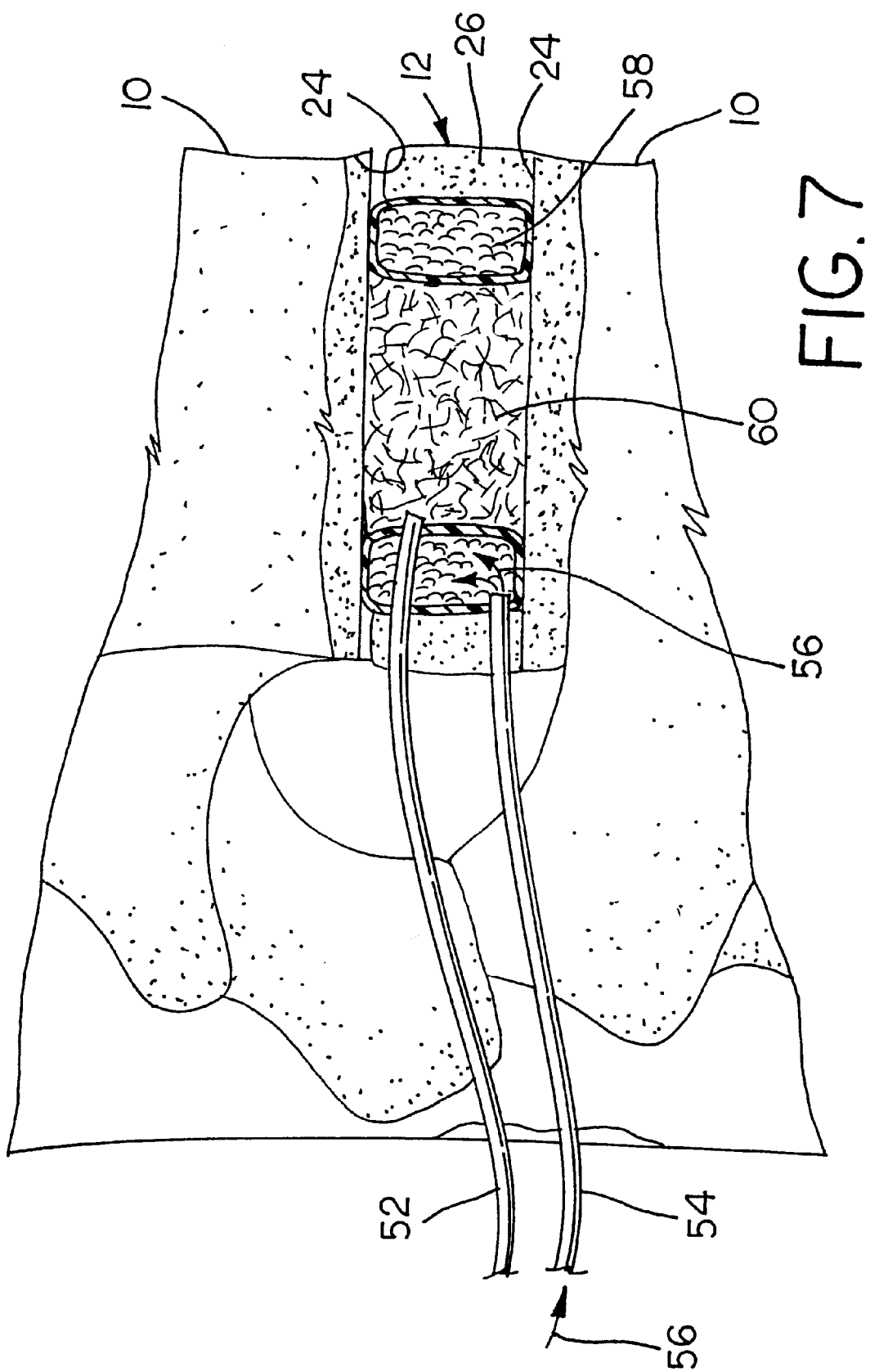
FIG. 7 is a side, sectional view illustrating the bag being filled to a second predetermined amount after injection of bone particles.
Figure 8:
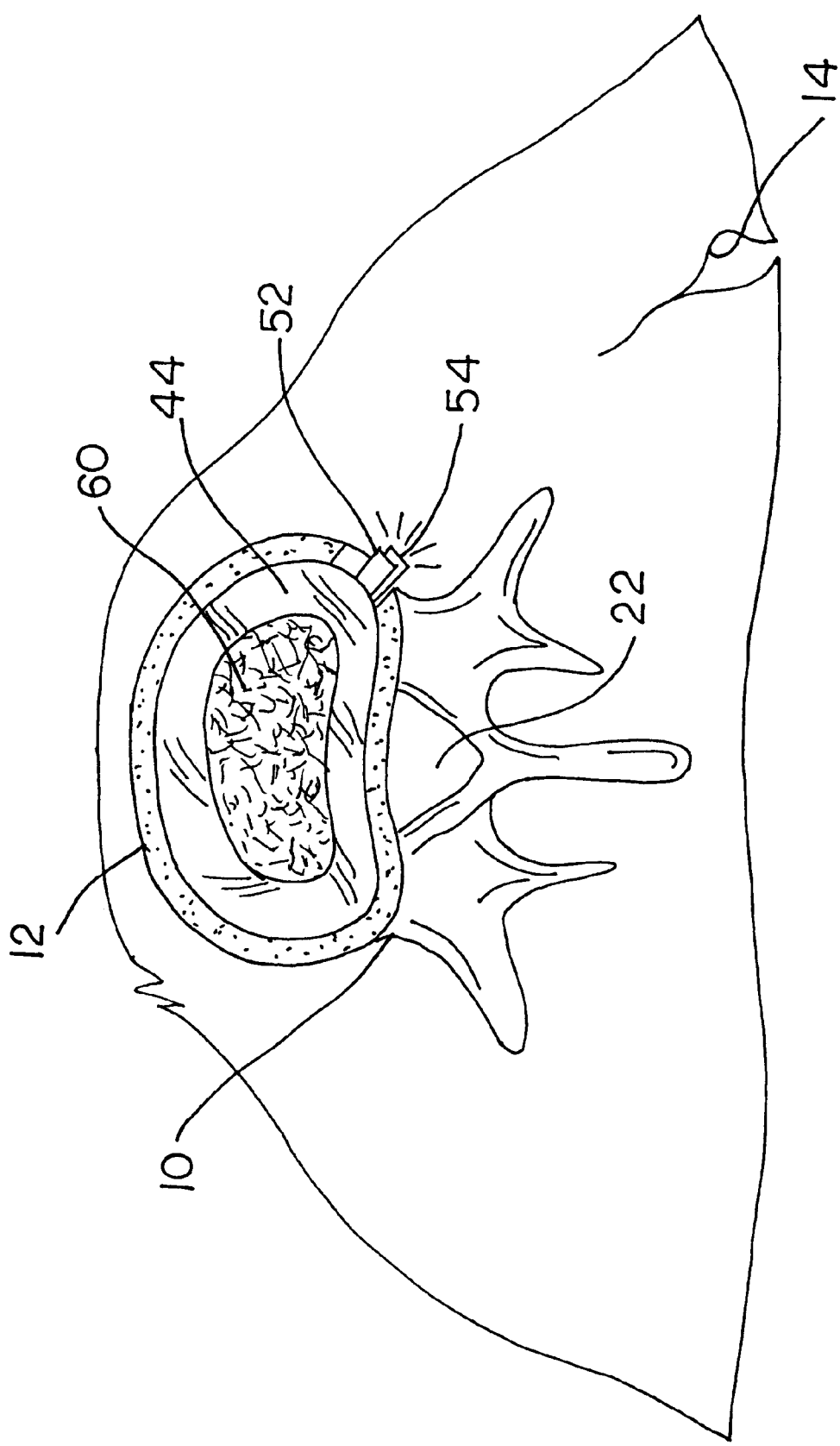
FIG. 8 is a fragmentary, sectional view with the orthopaedic implant implanted within a disc and the incision being closed.
Figure 9:
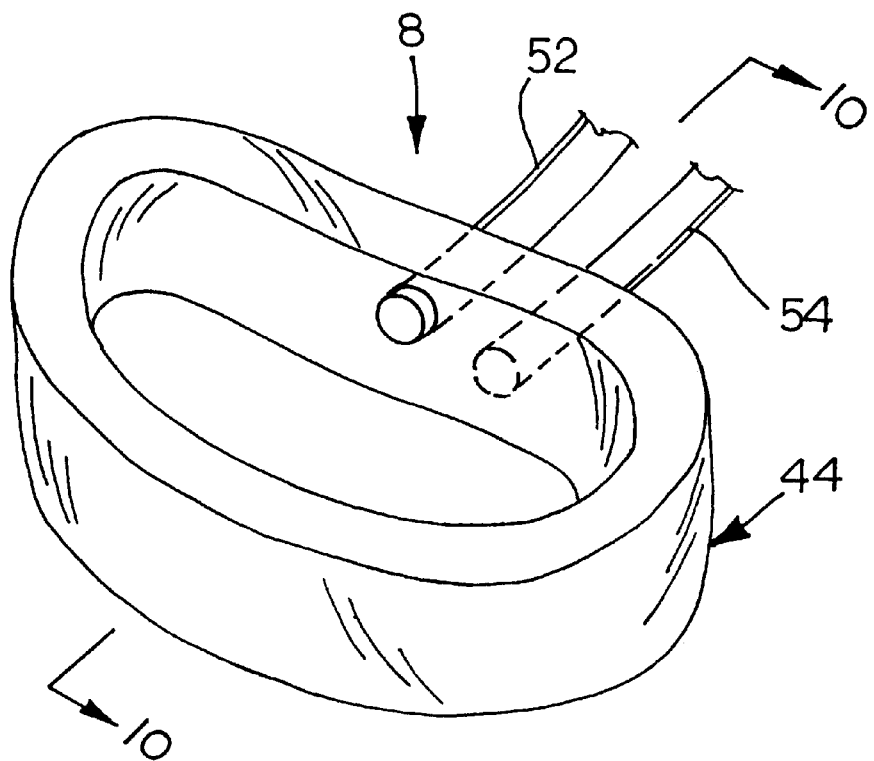
FIG. 9 is a perspective view of the bag shown in FIGS. 4–9.
Figure 10:
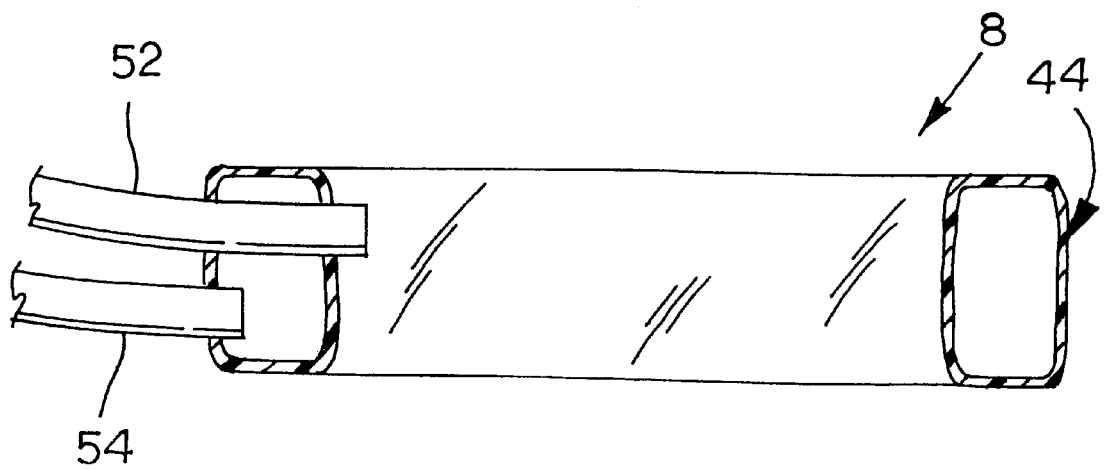
FIG. 10 is a side, sectional view of the bag shown in FIGS. 4–10.

A bone graft in the form of bone particles 60 is then injected through first fill hose 52 into the portion of cavity 42 surrounded by bag 44 (FIG. 7), as indicated by arrows 62. It should be understood that a bone substitute material can also be used. In the embodiment shown, bone particles 60 are suspended within a liquid such as synthetic bone substitute. The bone particle and suspension liquid is injected through first fill hose 52 and into cavity 42 until the portion of cavity 42 surrounded by bag 44 is substantially filled as shown in FIG. 7. Thereafter, bone particles 60 are retained within cavity 42 and additional polymer 58 is injected into bag 44 (FIG. 8). Polymer 58 is injected into bag 44 to a second predetermined amount causing expansion of bag 44. Bag 44 expands in an axial direction (relative to disc 12) and contacts end plates 24. Additionally, bag 44 expands in a radially inward direction causing radial compression and axial expansion of bone particles 60 within cavity 42. The ligaments and tendons surrounding vertebrae 10 may thus be retensioned by axially expanding bone particles 60 therebetween. Additionally, the fusion area is provided with a large contact area since substantially all of the area contacted by bone particles 60 and bag 44 forms a load bearing member. The polymer compound 58 within bag 44, as well as the polymer surrounding and carrying bone particles 60 may be cured to a load bearing state in a relatively fast manner. For example, the polymer compound may be cured with X-ray energy or a chemical catalyst. Thus, in addition to being minimally evasive, the patient is able to quickly load the spine through sitting, standing, etc. after curing of the polymer within orthopaedic implant 8. First fill hose 52 and second fill hose 54 are cut from orthopaedic implant 8, as indicated in FIG. 9, and incision 14 is closed using suitable closure techniques.

From the foregoing description, it can be seen that the present invention provides an orthopaedic implant 8 which may be easily implanted within a disc 12 with minimal evasive surgical procedures. The curing of the polymer within the bag between the adjacent vertebrae 10 occurs quickly and provides a large surface area for transfer of loads and a stable structure for the regrowth of bone between the vertebrae.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of fusing adjacent vertebrae in a spine, comprising the steps of:
   forming an access hole in an annulus of a disc between the adjacent vertebrae;
   removing the nucleus within the disc to form a cavity surrounded by said annulus;
   placing a generally annular bag within said cavity;
   filling said bag with a polymer;
   injecting bone particles into a portion of said cavity surrounded by said annular bag; and
   hardening said polymer.

2. The method of claim 1, wherein said filling step comprises filling said bag with said polymer to a first predetermined amount, and comprising the further step of filling said bag with said polymer to a second predetermined amount, said second filling step occurring after said injecting step.

3. The method of claim 2, wherein said second filling step compresses said bone particles in a radially inward direction into a column, and expands said column in an axial direction.

4. The method of claim 3, wherein said expansion of said bone particles in said axial direction loads said bone particles against an end plate of each respective said adjacent vertebrae.

5. The method of claim 3, wherein said second filling step provides height adjustment of said disc between said adjacent vertebrae.

6. The method of claim 1, wherein said bone particles comprise bone chips.

7. The method of claim 1, wherein said bone particles are suspended within a matrix.

8. The method of claim 1, wherein said forming step comprises forming said access hole in a side of said disc.

9. The method of claim 1, wherein said removing step comprises evacuating said nucleus from said disc.

10. The method of claim 1, wherein said placing step comprises the sub-steps of:
    folding said bag;
    inserting said folded bag within a pre-load tube;
    inserting at least an end of said pre-load tube into said cavity; and pushing said folded bag from said pre-load tube into said cavity.

11. The method of claim 1, wherein said filling step comprises injecting said polymer under pressure into said bag.

12. The method of claim 11, wherein said bag is expandable under said pressure.

13. The method of claim 1, wherein said polymer comprises a curable polymer.

14. The method of claim 13, wherein said polymer is curable with one of thermal energy, light energy, X-ray energy and a chemical catalyst.

15. The method of claim 14, wherein said hardening step comprises hardening said polymer with a chemical catalyst.

16. The method of claim 1, wherein said bag comprises a porous bag allowing some of said polymer to pass therethrough.

17. An orthopaedic implant for implanting between adjacent vertebrae in a spine, comprising:

a generally annular bag; and a hardened polymer within said bag.

18. The orthopaedic implant of claim 17, further comprising a fill tube connected with said bag for injecting said polymer into said bag.

19. The orthopaedic implant of claim 17, wherein said polymer comprises a curable polymer.

20. The orthopaedic implant of claim 19, wherein said polymer is curable with one of thermal energy, light energy, X-ray energy and a chemical catalyst.

21. The orthopaedic implant of claim 20, wherein said polymer comprises polymethylmethacrylate.

22. The orthopaedic implant of claim 17, wherein said bag comprises a porous bag allowing some of said polymer to pass therethrough.

* * * * *